United States Patent
McCain et al.

(10) Patent No.: US 12,156,558 B2
(45) Date of Patent: Dec. 3, 2024

(54) MULTILAYER GARMENTS WORN DURING WOUND CARE

(71) Applicant: CREATE TO OVERCOME LLC, Kirkland, WA (US)

(72) Inventors: Aisha Michelle McCain, El Cerrito, CA (US); Annemarie Noelle Sheets, Berkeley, CA (US)

(73) Assignee: CREATE TO OVERCOME LLC, Kirkland, WA (US)

( * ) Notice: Subject to any disclaimer, the term of this patent is extended or adjusted under 35 U.S.C. 154(b) by 165 days.

(21) Appl. No.: 16/948,466

(22) Filed: Sep. 20, 2020

(65) Prior Publication Data

US 2021/0085007 A1    Mar. 25, 2021

Related U.S. Application Data

(60) Provisional application No. 62/903,612, filed on Sep. 20, 2019.

(51) Int. Cl.
*A61F 13/00* (2024.01)
*A41D 31/02* (2019.01)
(Continued)

(52) U.S. Cl.
CPC ........... *A41D 31/125* (2019.02); *A41D 31/02* (2013.01); *A61F 13/00987* (2013.01);
(Continued)

(58) Field of Classification Search
CPC ......... A61F 13/00029; A61M 2210/12; A61M 25/0074; A61M 1/00; A61M 1/3655;
(Continued)

(56) References Cited

U.S. PATENT DOCUMENTS

| 1,444,750 A | 2/1923 | Moore | 2/94 |
| 1,520,962 A | 12/1924 | North | 2/102 |

(Continued)

FOREIGN PATENT DOCUMENTS

| ES | 2932654 T3 * | 1/2023 | ....... A61F 13/00051 |
| WO | WO-2007030601 A2 * | 3/2007 | ....... A61F 13/00055 |

(Continued)

OTHER PUBLICATIONS

ES 2932654-T3 translation (Year: 2023).*

*Primary Examiner* — Kim M Lewis
(74) *Attorney, Agent, or Firm* — Cynthia S. Lamon; Lamon Patent Services

(57) ABSTRACT

A wound recovery garment includes a multilayer fabric. The multilayer fabric comprises a first layer, a second layer, and a third layer. The multilayer fabric draws moisture from the skin tissues, including wounded or burned tissue recovering from trauma. The first layer removes moisture from wounded tissue without sticking to skin. The first layer is formed from compressive, elastic material that supplies compression forces to tissue. The second layer is an absorbent layer that receives the moisture from the first layer and stores tissue moisture in a sponge-like fashion. The second layer is disposed between the first layer and the third layer. The third layer is an exterior layer and is visible to outside viewers. No body fluid or blood leaks through the third layer. Individuals recovering from trauma are able to comfortably go outside without being concerned with body fluids soaking through and being visible to others.

11 Claims, 5 Drawing Sheets

(51) Int. Cl.
*A41D 31/12* (2019.01)
*A61F 13/06* (2006.01)
*A61F 13/08* (2006.01)
*A61F 13/10* (2006.01)
*A61F 13/14* (2006.01)
*B32B 5/02* (2006.01)
*B32B 5/26* (2006.01)
*A61N 1/04* (2006.01)

(52) U.S. Cl.
CPC .......... *A61F 13/061* (2013.01); *A61F 13/064* (2013.01); *A61F 13/066* (2013.01); *A61F 13/068* (2013.01); *A61F 13/08* (2013.01); *A61F 13/104* (2013.01); *A61F 13/105* (2013.01); *A61F 13/107* (2013.01); *A61F 13/143* (2013.01); *A61F 13/148* (2013.01); *B32B 5/024* (2013.01); *B32B 5/26* (2013.01); *A61F 2013/00119* (2013.01); *A61F 2013/00127* (2013.01); *A61F 2013/00157* (2013.01); *A61F 2013/00187* (2013.01); *A61F 2013/0028* (2013.01); *A61F 2013/00285* (2013.01); *A61N 1/0468* (2013.01); *B32B 2307/726* (2013.01); *B32B 2437/00* (2013.01)

(58) Field of Classification Search
CPC ................ A61M 1/60; A61M 16/0688; A61M 2016/003; A61M 2025/0008; A61M 2202/0275; A61M 2205/02; A61M 2205/3584; A61M 2209/086; A61M 2210/0668; A61M 2230/201; A61M 2230/202; A61M 2230/432; A61M 2230/435; A61M 5/1723; A61M 15/08; A61M 16/00; A61M 16/0858; A61M 2005/1726; A61M 2016/0661; A61M 2025/0286; A61M 2025/1075; A61M 2205/582; A61M 2205/70; A61M 2210/0606; A61M 25/0009; A61M 25/0082; A61M 3/0204; A61M 3/0241; A61M 3/0258; A61M 3/0287; A61M 5/178; A61M 1/3661; A61M 1/604; A61M 1/918; A61M 16/0694; A61M 16/0866; A61M 2037/0046; A61M 2210/0637; A61M 5/00; A61M 5/422; A61M 5/427; A61M 1/742; A61M 1/76; A61M 1/81; A61M 16/0003; A61M 16/0069; A61M 16/08; A61M 16/0833; A61M 16/1065; A61M 2005/1585; A61M 2025/0226; A61M 2025/0687; A61M 2039/0276; A61M 2202/064; A61M 2205/3313; A61M 2205/3606; A61M 2205/505; A61M 2210/0662; A61M 2210/1085; A61M 25/008; A61M 3/0279; A61M 5/002; A61M 1/064; A61M 1/602; A61M 1/964; A61M 2025/0002; A61M 2025/006; A61M 2025/1059; A61M 2025/1084; A61M 2025/1093; A61M 2205/21; A61M 2205/7545; A61M 2206/10; A61M 2210/0612; A61M 2230/20; A61M 25/005; A61M 25/1006; A61M 25/1011; A61M 25/10182; A61M 1/3656; A61M 11/042; A61M 16/161; A61M 2039/0261; A61M 2202/0496; A61M 2205/7527; A61M 2210/06; A61M 2210/1092; A61M 2210/1096; A61M 2230/04; A61M 25/003; A61M 5/14; A61M 5/445; A61M 1/14; A61M 16/049; A61M 16/109; A61M 2005/3022; A61M 2025/0019; A61M 2025/0206; A61M 2039/0273; A61M 2202/02; A61M 2202/068; A61M 2205/3375; A61M 2205/75; A61M 2210/0625; A61M 2210/1067; A61M 25/09; A61M 5/16845; A61M 5/30; A61M 5/31; A61M 1/06; A61M 1/0697; A61M 1/3653; A61M 1/772; A61M 11/041; A61M 15/009; A61M 15/06; A61M 16/0644; A61M 19/00; A61M 2005/3117; A61M 2016/0018; A61M 2016/0033; A61M 2025/0081; A61M 2025/0213; A61M 21/02; A61M 2202/0216; A61M 2205/051; A61M 2205/075; A61M 2205/52; A61M 2205/587; A61M 2205/6054; A61M 2205/6081; A61M 2205/8237; A61M 2205/8262; A61M 2210/083; A61M 2210/1007; A61M 2230/208; A61M 25/0102; A61M 25/065; A61M 39/0208; A61M 39/24; A61M 5/16827; A61M 1/3659; A61M 15/0051; A61M 16/0057; A61M 16/024; A61M 16/105; A61M 16/1095; A61M 16/22; A61M 2005/1588; A61M 2005/3131; A61M 2025/0063; A61M 2025/09125; A61M 2025/1031; A61M 2037/0038; A61M 2039/0054
USPC .................................................... 602/58, 79
See application file for complete search history.

(56) References Cited

U.S. PATENT DOCUMENTS

| | | | |
|---|---|---|---|
| 3,055,133 A | 9/1962 | Anderson | 40/586 |
| 3,343,537 A * | 9/1967 | Graham | A61F 13/143 602/42 |
| 4,667,665 A * | 5/1987 | Blanco | B29C 66/2442 604/378 |
| 5,142,702 A | 9/1992 | Piloian | 2/102 |
| 6,574,800 B1 | 6/2003 | Leger et al. | A41D 1/22 |
| 6,664,434 B2 * | 12/2003 | Cominsky | A61F 15/004 602/61 |
| 7,004,922 B1 * | 2/2006 | Shesol | A61D 9/00 119/856 |
| 7,396,272 B1 | 7/2008 | Newlen | 450/54 |
| 7,823,221 B2 | 11/2010 | Green | 2/114 |
| 7,887,501 B2 * | 2/2011 | Riordan | A61F 13/12 424/445 |
| 8,898,812 B2 * | 12/2014 | Thompson | A41D 27/13 2/53 |
| D764,145 S | 8/2016 | Mathews | |
| 9,433,544 B1 * | 9/2016 | Ross | A41D 15/04 |
| 10,179,186 B2 | 1/2019 | Moreland et al. | A61F 13/08 |
| 10,188,160 B1 | 1/2019 | McCain | A41D 13/1245 |
| 10,264,831 B1 | 4/2019 | Hemker | A41D 13/1245 |
| 10,391,740 B2 | 8/2019 | Bailey et al. | B32B 5/26 |
| 10,603,220 B2 * | 3/2020 | Ahmed | A61F 13/00029 |
| 2004/0226073 A1 | 11/2004 | McCullar et al. | 2/114 |
| 2006/0156450 A1 | 7/2006 | McGrath | 2/114 |
| 2006/0253954 A1 | 11/2006 | Music | 2/115 |
| 2007/0113316 A1 | 5/2007 | King | 2/102 |
| 2007/0271672 A1 | 11/2007 | Lentini | 2/69 |
| 2008/0000006 A1 | 1/2008 | Ochoa et al. | 2/114 |
| 2008/0184455 A1 | 8/2008 | Blume | 2/114 |
| 2008/0312615 A1 | 12/2008 | Hunter | 604/345 |
| 2010/0107294 A1 | 5/2010 | Gillian | 2/49.5 |
| 2010/0205720 A1 | 8/2010 | Ortega Astor | 2/247 |
| 2011/0041231 A1 | 2/2011 | Behrens et al. | 2/69 |
| 2011/0302703 A1 | 12/2011 | Silverberg | 2/457 |
| 2012/0030851 A1 | 2/2012 | Kinder et al. | 2/69 |

(56) References Cited

U.S. PATENT DOCUMENTS

| | | | |
|---|---|---|---|
| 2012/0090072 A1 | 4/2012 | Oprandi et al. | 2/114 |
| 2012/0291179 A1 | 11/2012 | Shea | 2/102 |
| 2013/0116613 A1* | 5/2013 | Entler | A61D 9/00 602/79 |
| 2015/0216242 A1 | 8/2015 | Evans et al. | A41D 12/1245 |
| 2015/0296896 A1 | 10/2015 | Laguna | A41C 3/0064 |
| 2015/0366276 A1 | 12/2015 | Kuzmanovski | A41D 13/1245 |
| 2016/0219951 A1 | 8/2016 | Schickel | A41D 13/1236 |
| 2016/0331049 A1 | 11/2016 | Roberson et al. | A41D 13/1245 |
| 2018/0003579 A1 | 1/2018 | Esposito et al. | G01L 5/0052 |
| 2019/0159533 A1 | 5/2019 | James et al. | A41D 13/1245 |

FOREIGN PATENT DOCUMENTS

| | | | | |
|---|---|---|---|---|
| WO | WO-2015140564 A1 * | 9/2015 | | A61F 13/0209 |
| WO | WO2020145963 | 7/2021 | | |

\* cited by examiner

MULTILAYER GARMENTS WORN DURING WOUND CARE

CROSS REFERENCE TO RELATED APPLICATIONS

This application claims the benefit under 35 U.S.C. § 119 from U.S. Provisional Patent Application Ser. No. 62/903,612, entitled "Multilayer Garments Worn During Wound Care," filed on Sep. 20, 2019, the subject matter of which is incorporated herein by reference.

TECHNICAL FIELD

The present invention relates generally to garments and clothing.

SUMMARY

A wound recovery garment includes a multilayer fabric. The multilayer fabric comprises a first layer, a second layer, and a third layer. The multilayer fabric draws moisture from the skin tissues, including wounded or burned tissue recovering from trauma. The first layer removes moisture from wounded tissue without sticking to skin. The first layer is formed from compressive, elastic material that supplies compression forces to wounded tissue. The second layer is an absorbent layer that receives the moisture from the first layer and stores tissue moisture in a sponge-like fashion. The second layer is disposed between the first layer and the third layer. The third layer is an exterior layer and is visible to outside viewers. No body fluid or blood leaks through the third layer. Individuals recovering from trauma are able to comfortably go outside without being concerned with body fluids soaking through and being visible to others.

The foregoing is a summary and thus contains, by necessity, simplifications, generalizations and omissions of detail; consequently it is appreciated that the summary is illustrative only. Still other methods, and structures and details are set forth in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

DETAILED DESCRIPTION

Reference will now be made in detail to background examples and some embodiments of the invention, examples of which are illustrated in the accompanying drawings.

Figure 1:
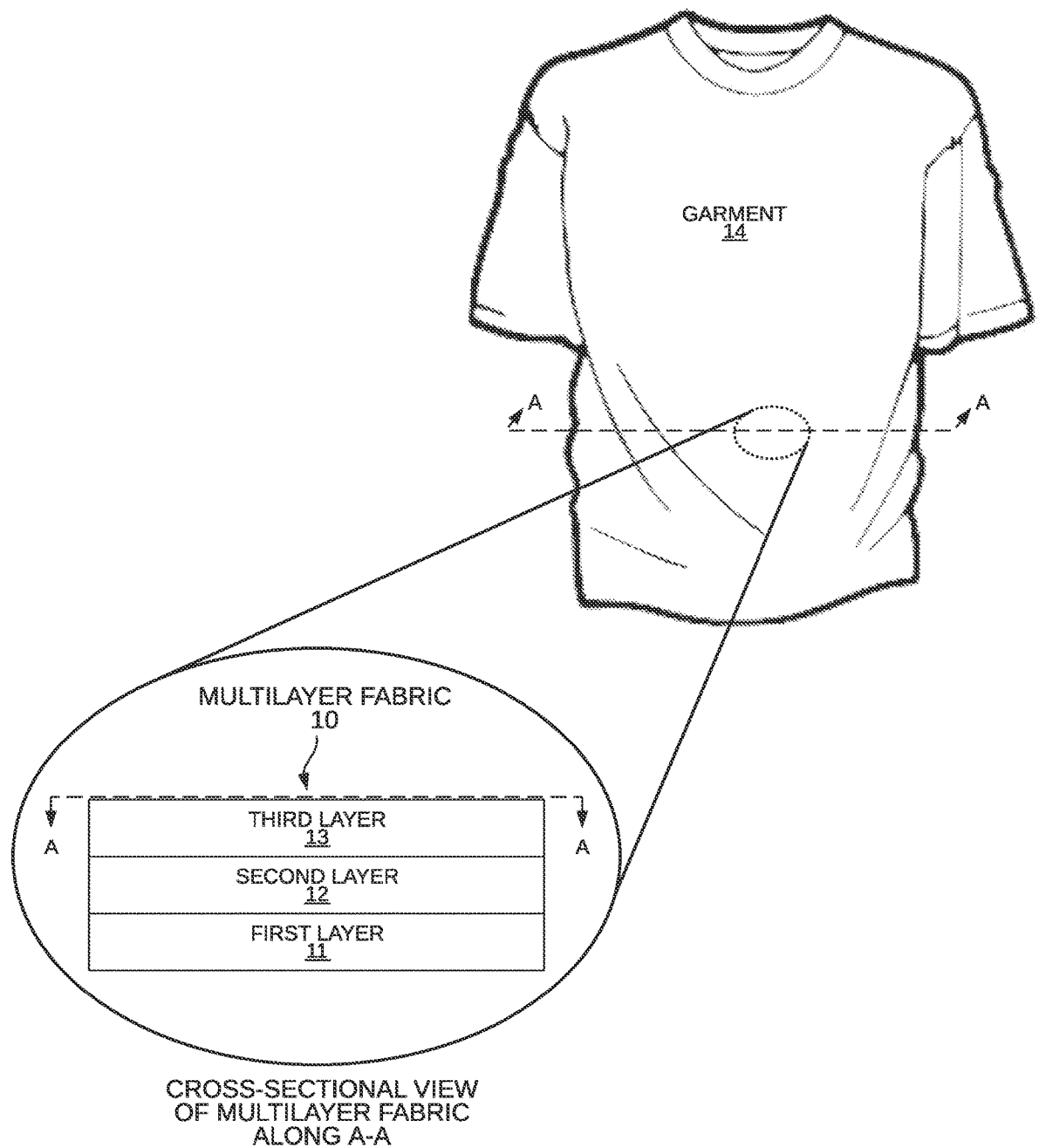
FIG. 1 a diagram of a cross-sectional view of multilayer fabric 10.

FIG. 1 a diagram of a cross-sectional view of multilayer fabric 10. The multilayer fabric 10 comprises a first layer 11, a second layer 12, and a third layer 13. The multilayer fabric 10 is part of a garment 14. In one embodiment, the multilayer fabric 10 extends throughout the entirety of the garment 14. In another embodiment, only parts of the garment 14 have the multilayer fabric 10.

The multilayer fabric 10 draws moisture from the skin tissues, including wounded or burned tissue recovering from trauma. The first layer 11 has a tissue contact surface that is identified by reference numeral 19 in FIG. 3. The first layer 11 draws moisture away from wounded tissue and transfers the moisture into the second layer 12. The second layer 12 is an absorbent layer and receives and stores tissue moisture received via the first layer 11. The second layer 12 is disposed between the first layer 11 and the third layer 13. The third layer 13 is an exterior layer. The third layer 13 has an external environment contact surface and is visible to an outer environment.

The garment 14 is any garment that can be worn against skin. The garment 14 assists with individuals recovering from wounds or burns to heal. The garment 14 allows wounds or damaged tissue to breathe and heal without moisture. The garment 14 does not stick to wounds and absorbs body fluid or blood without leaking thru to outer layers. The garment 14 permits individuals with wounds to go outside in public without feeling self-conscious or embarrassed. In the case of conventional garments, body fluids tend to leak through conventional garments. On the other hand, the novel garment 14 with the multilayer fabric 10 prevents body fluids and blood from leaking through and being visible to external environments.

Figure 2:
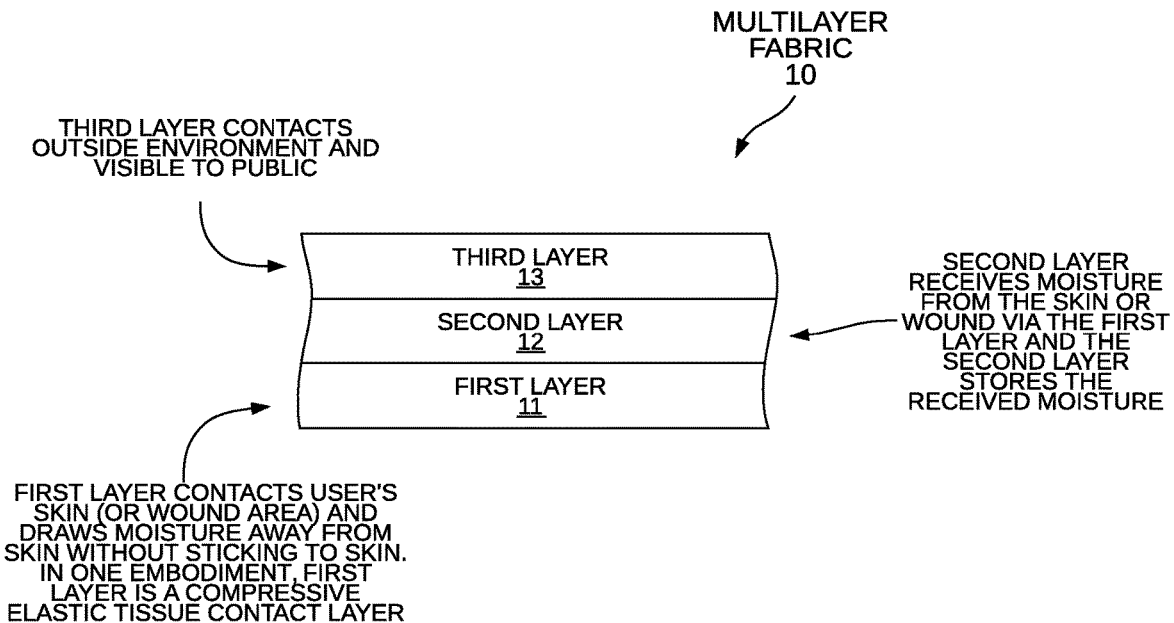
FIG. 2 a diagram of a cross-sectional view of multilayer fabric 10 showing the various layers of fabric 10.

FIG. 2 a diagram of a cross-sectional view of multilayer fabric 10 showing the various layers of fabric 10. A first surface of the second layer 12 contacts a surface of the first layer 11. A second surface of the second layer 12 contacts a surface of the third layer 13. In one embodiment, the layers are mechanically attached together through a stitching process. In another embodiment, the layers are adhesively attached together through an adhesion process.

The first layer 11 is a smooth fabric material that is cool to touch and does not stick to wounded tissue or skin. The first layer 11 wicks moisture away from wounded tissue or skin into the interior second layer 12. In one embodiment, the first layer 11 is formed from a poly and spandex material. For example, the first layer 11 is formed from 90% poly material and 10% spandex material. In another embodiment, the first layer 11 is formed from a poly lycra tricot fabric. For example, the first layer 11 is formed from 73% poly material and 27% lycra material.

The second layer 12 holds and collects the moisture from wounded tissue or skin. The second layer 12 is an absorbent layer of fabric. The second layer 12 operates as a sponge to absorb the moisture received onto the first layer 11 from the skin. In one embodiment, the second layer 12 is formed from cotton fibers. For example, the second layer 12 is formed from a 3D Cotton Dimple. In another embodiment, the second layer 12 is formed from bamboo fibers. For example, the second layer 12 is formed from a Bamboo Lining Fleece.

The third layer 13 is an outer garment layer. The third layer 13 is viewed as a regular garment to outside viewers. The first layer 11 and the second layer 12 are not visible from the outside. The first layer 11 and the second layer 12 prevent body fluid or blood from leaking through to the third layer 13. In one embodiment, the third layer 13 is formed from a woven fabric. In another embodiment, the third layer 13 is formed from a knit fabric.

Figure 3:
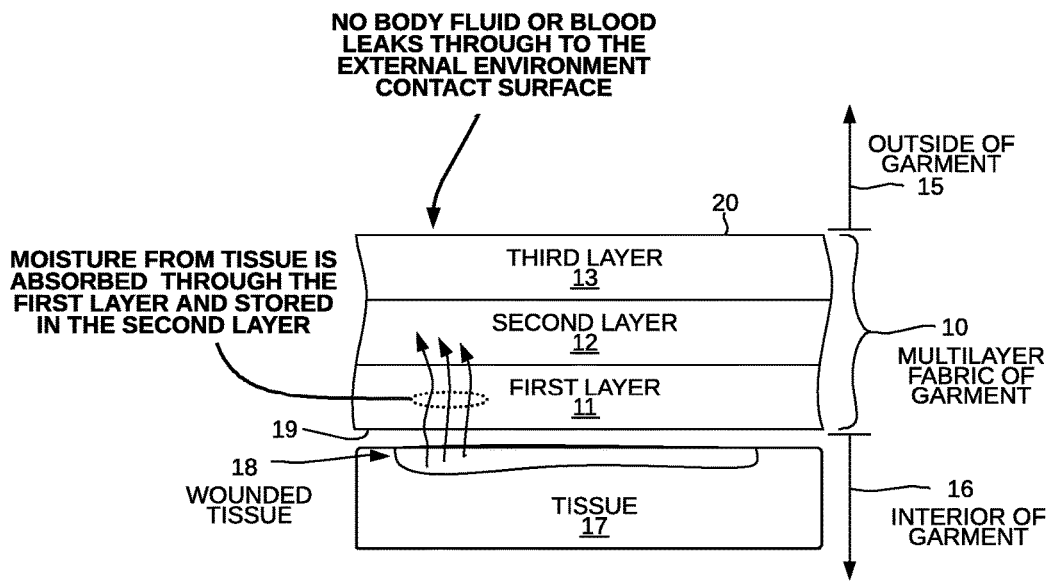
FIG. 3 is a diagram of a cross-sectional view of multilayer fabric 10 showing how moisture is absorbed and stored within the fabric 10.

FIG. 3 is a diagram of a cross-sectional view of multilayer fabric 10 showing how moisture is absorbed and stored within the fabric 10. The first layer 11 is disposed adjacent to the tissue of the wearer 17. The third layer 13 is exposed to an outside environment 15. The third layer 13 has an external environment contact surface 20. The first layer 11 has a tissue contact surface 19. The tissue contact surface 19 is disposed within an interior 16 of the garment 14. Part or all of the tissue 17 may contact the first layer 11. The tissue 17 optionally has a wounded or burn area 18 that is recovering from trauma. In operation, the moisture from the tissue 17 and wound 18 is absorbed through the first layer 11 and stored in the second layer 12. No body fluid or blood leaks through to the external environment contact surface 20.

Figure 4:
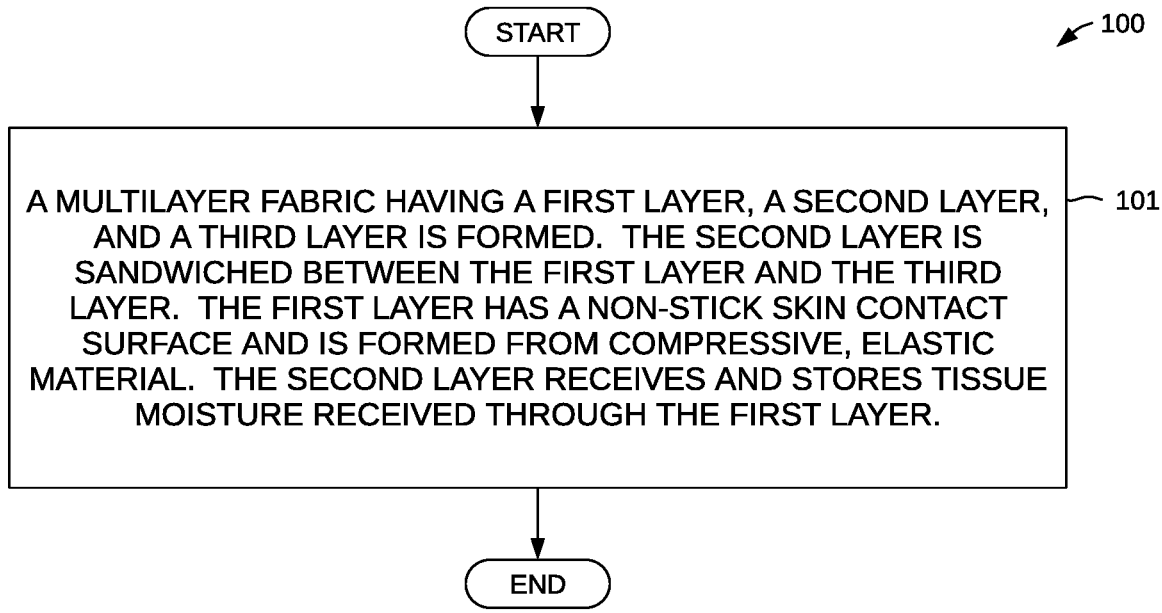
FIG. 4 is a diagram of a flowchart 100 of a method in accordance with another novel aspect.

FIG. 4 is a diagram of a flowchart 100 of a method in accordance with another novel aspect. In a first step (101), a multilayer fabric having a first layer, a second layer, and a third layer is formed. The second layer is sandwiched between the first layer and the third layer. The first layer has a non-stick skin contact surface and is formed from compressive, elastic material. The second layer receives and stores tissue moisture received through the first layer.

Figure 5:
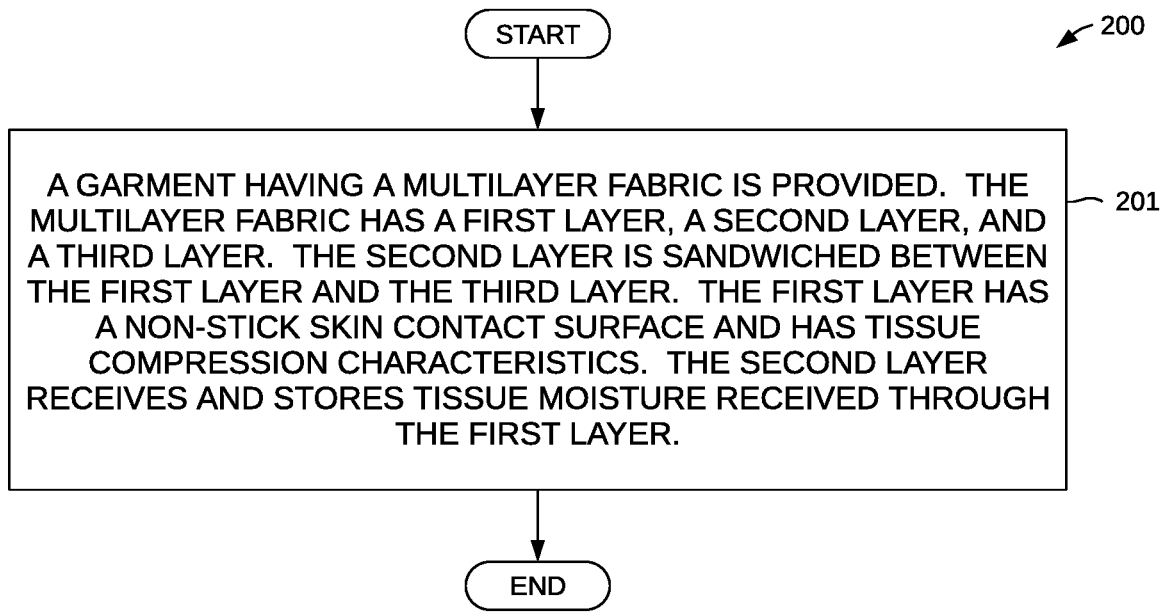
FIG. 5 is a diagram of a flowchart 200 of a method in accordance with another novel aspect.

FIG. 5 is a diagram of a flowchart 200 of a method in accordance with another novel aspect. In a first step (201), a garment having a multilayer fabric is provided. The multilayer fabric has a first layer, a second layer, and a third layer. The second layer is sandwiched between the first layer and the third layer. The first layer has a non-stick skin contact surface and has tissue compression characteristics. The second layer receives and stores tissue moisture received through the first layer.

Figure 6:
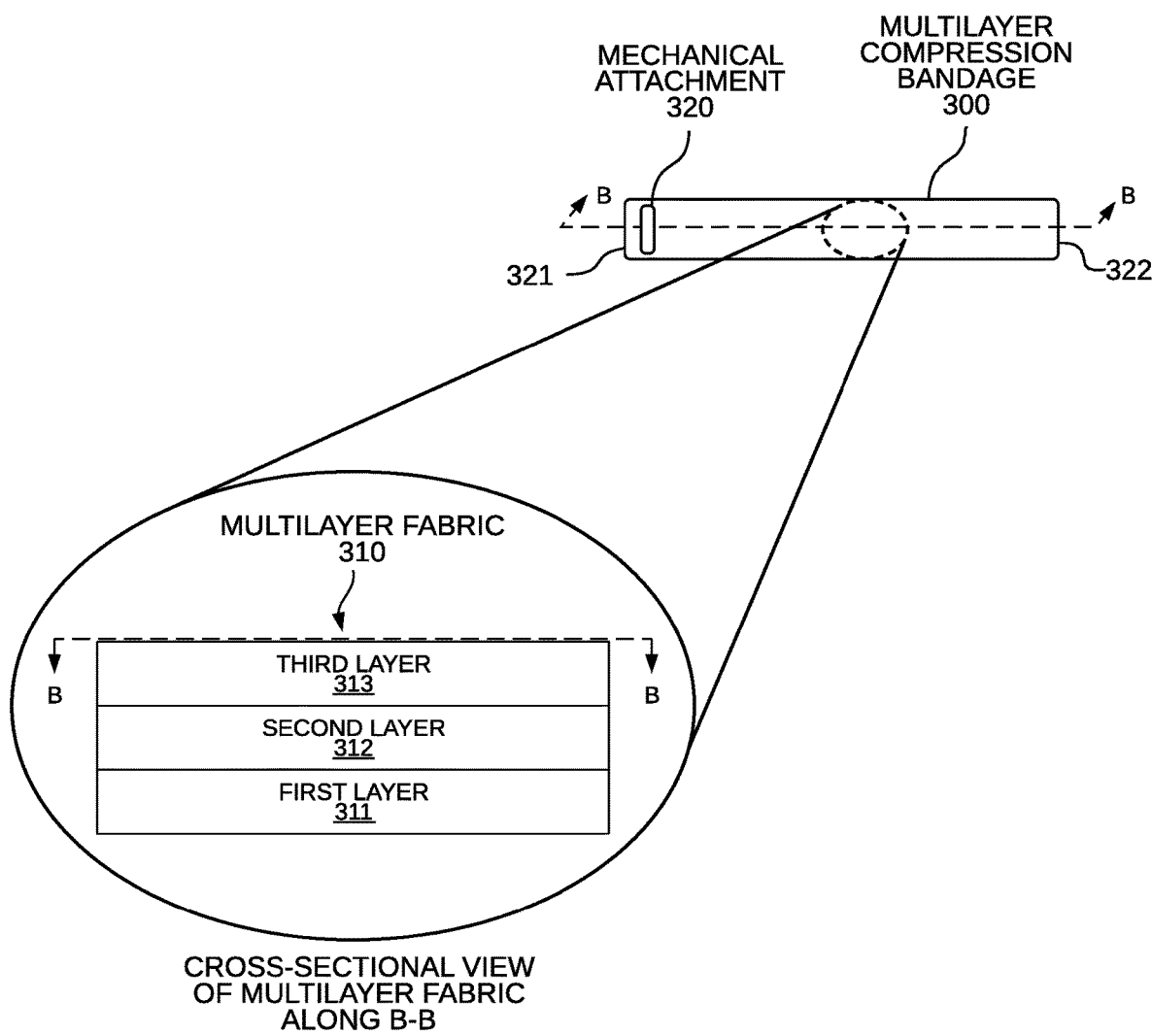
FIG. 6 is a diagram of a multilayer compression bandage 300 in accordance with one embodiment.

FIG. 6 is a diagram of a multilayer compression bandage 300 in accordance with one embodiment. The multilayer compression bandage 300 comprises a multilayer fabric 310 having at least three layers, at least one mechanical attachment 320, a first end 321, and a second end 322. The multilayer fabric 310 includes first layer 311, a second layer 312, and a third layer 313. In one embodiment, the multilayer fabric 310 extends throughout the entirety of the bandage 300. In another embodiment, only parts of the bandage 300 have the multilayer fabric 310.

In operation, the multilayer compression bandage 300 is applied to tissue of a user. The multilayer compression bandage 300 is wrapped around the tissue of the user. The mechanical attachment 320 is used to retain the multilayer compression bandage 300 in place and apply compression to the tissue. After the multilayer compression bandage 300 is wrapped around the tissue and set at a desired location and compression, the mechanical attachment 321 is attached to the multilayer compression bandage 300.

The multilayer fabric 310 draws moisture from the skin tissues, including wounded or burned tissue recovering from trauma. The first layer 311 has a tissue contact surface. The first layer 311 draws moisture away from wounded tissue and transfers the moisture into the second layer 312. The second layer 312 is an absorbent layer and receives and stores tissue moisture received via the first layer 311. The second layer 312 is disposed between the first layer 311 and the third layer 313. The third layer 313 is an exterior layer. The third layer 313 has an external environment contact surface and is visible to an outer environment.

In this example, the multilayer compression bandage 300 shown in FIG. 6 has a rectangular shape. It is appreciated that the multilayer compression bandage 300 is any type of bandage or medical wound covering that can be worn against skin. The multilayer compression bandage 300 assists with individuals recovering from wounds or burns to heal. The multilayer compression bandage 300 allows wounds or damaged tissue to breathe and heal without moisture. The multilayer compression bandage 300 does not stick to wounds and absorbs body fluid or blood without leaking thru to outer layers. The multilayer compression bandage 300 permits individuals with wounds to go outside in public without feeling self-conscious or embarrassed. The multilayer fabric 10 prevents body fluids and blood from leaking through and being visible to external environments and also applies compressive forces to recovering tissue.

The first surface of the second layer 312 contacts a surface of the first layer 311. A second surface of the second layer 312 contacts a surface of the third layer 313. In one embodiment, the layers are mechanically attached together through a stitching process. In another embodiment, the layers are adhesively attached together through an adhesion process.

The first layer 311 is a smooth fabric material that is cool to touch and does not stick to wounded tissue or skin. The first layer 311 wicks moisture away from wounded tissue or skin into the interior second layer 312. In one embodiment, the first layer 311 is formed from a poly and spandex material. For example, the first layer 311 is formed from 90% poly material and 10% spandex material. In another embodiment, the first layer 311 is formed from a poly lycra tricot fabric. For example, the first layer 311 is formed from 73% poly material and 27% lycra material.

The second layer 312 holds and collects the moisture from wounded tissue or skin. The second layer 312 is an absorbent layer of fabric. The second layer 312 operates as a sponge to absorb the moisture received onto the first layer 311 from the skin. In one embodiment, the second layer 312 is formed from cotton fibers. For example, the second layer 312 is formed from a 3D Cotton Dimple. In another embodiment, the second layer 312 is formed from bamboo fibers. For example, the second layer 312 is formed from a Bamboo Lining Fleece.

The third layer 313 is an outer layer that contacts the environment. The third layer 313 is selected to be visually appealing and not appear as a medical type of bandage. The first layer 311 and the second layer 312 are not visible from the outside. The first layer 311 and the second layer 312 prevent body fluid or blood from leaking through to the third layer 313. In one embodiment, the third layer 313 is formed from a woven fabric. In another embodiment, the third layer 313 is formed from a knit fabric.

Figure 7:
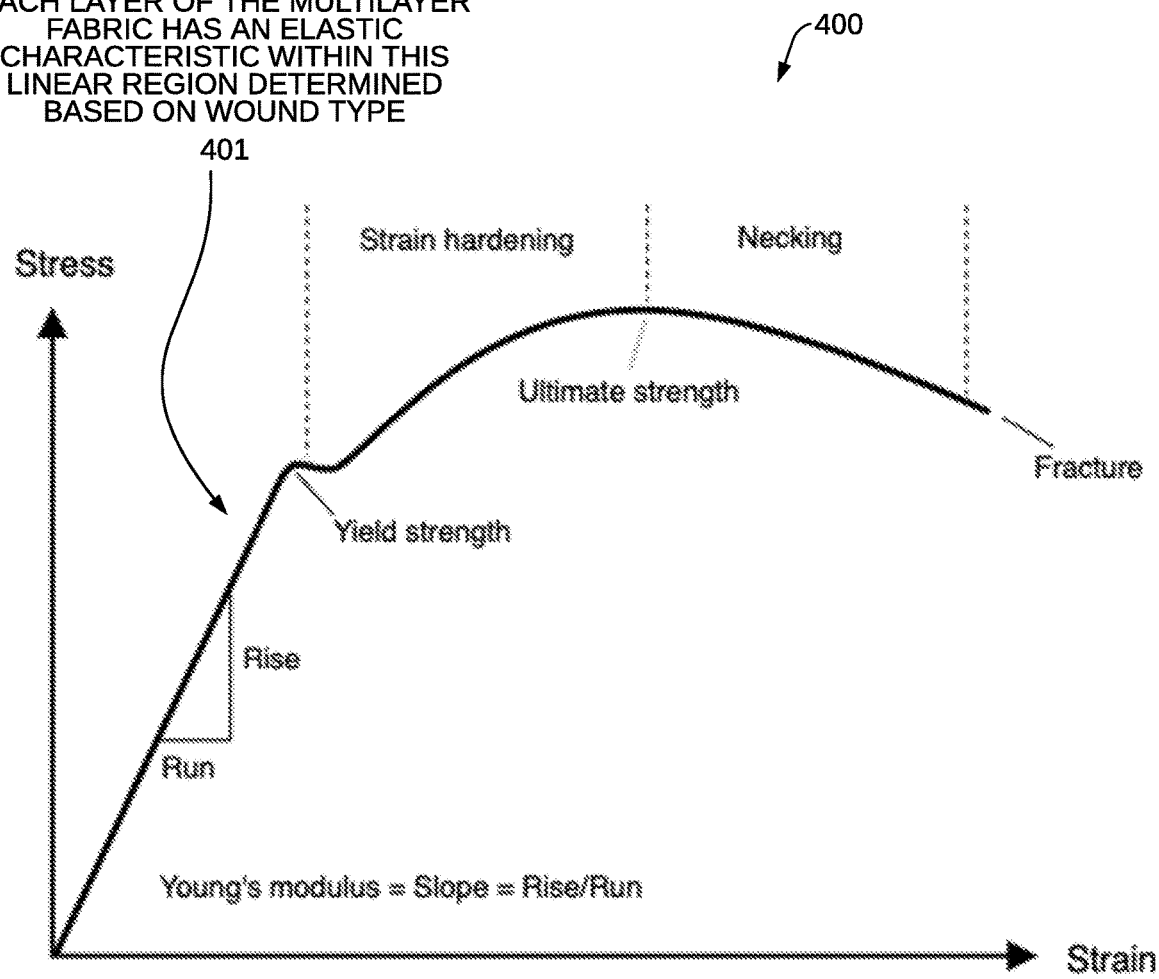
FIG. 7 is a graph 400 showing how selection of material for the multilayer fabrics 10 and 310 having desired elasticity improves wound treatment outcomes.

FIG. 7 is a graph 400 showing how selection of material for the multilayer fabrics 10 and 310 having desired elasticity improves wound treatment outcomes. Reference numeral 401 identifies a linear region. Each layer of the multilayer fabrics 10 and 310 has an elastic characteristic within this linear region determined based on wound type. The layers of the multilayer fabrics 10 and 310 have elastic properties that provide sufficient compression to wounded tissue to protect tissue, avoid further injury, and enhance healing.

Wounds include acute and chronic disruption of the skin or mucous membranes from any cause whether traumatic, environmental, iatrogenic, or due to a medical condition. Wounds are extremely common and often need dressings or bandages, and frequent bandage changes. Bandages are often difficult to change without assistance. Tape and medical adhesives can cause skin damage. Plastic traps moisture against the skin. Dressings often stick painfully to wounds and may cause further damage. Dressings and bandages also tend to fall off with activity.

Elasticity of the multilayer fabric is desirable because it moves with a user's body. A multilayer fabric having elastic qualities is operable to hold dressings in place and provides compression forces on wounded tissue. Compression is desirable to limit or prevent swelling, to provide support to healing wounds, to promote hemostasis, to prevent or treat thrombosis, or to decrease pain. It is appreciated that applying compression forces to wounded tissue provides many additional medical benefits in addition to those presented herein.

Excessive or insufficient compression can be ineffectual or dangerous depending on underlying wound presentation. Conventional bandages typically tend to be difficult to apply, highly variable, very expensive, can lead to further skin damage or allergic reactions, or look characteristically medical ("like a mummy"). Clinical data indicates that medical outcomes are improved and healing hastened when patients recovering from trauma are not perceived as being ill in public settings.

In various embodiments, a multilayer fabric of at least three layers is provided as part of a garment or bandage. Each layer of the multilayer fabric has elastic properties specially designed in wrap-around style fashion for application to chest, abdomen, limbs, or other body parts. A first layer, or dressing layer, is applied directly to tissue. A second layer, or absorptive layer, draws and retains drainage from the dressing layer. A third layer, or bandage Layer, supports the other two layers and provides padding and protection from additional injury.

The novel multilayer fabric is usable to treat wounds in connection with sunburn, poison ivy/oak/sumac lymphedema, thrombophlebitis, insect bites, psoriasis, contact dermatitis, dialysis fistula, PICC line, post surgical sprain, strain, or injury, fatigue prevention, DVT, wound dehiscence, hernias, orthostatic hypotension, diabetic wounds, venous stasis wounds, arterial insufficiency, cardiogenic edema, Crohn's Disease, colostomy or ileostomy, urostomy, peritoneal dialysis catheter, pregnancy-related edema, postpartum C-section support, cellulitis, burn injuries, decrease scar formation, friable skin due to extremes of age, herpes zoster, bite or crush injuries, skin cancer, complex regional pain, neuropathic pain, topical medication, varicose veins, protection of pressure points prevent additional injury, and psychosocial improvement performance enhancement research.

In one embodiment, the multilayer fabric includes three and only three layers. The multilayer fabric includes a hook-and-loop fastener or hook-and-pile fastener to attach the multilayer fabric to human tissue.

In another embodiment, the multilayer fabric includes at least three layers. The multilayer fabric includes a hook-and-loop fastener or hook-and-pile fastener (such as VELCRO®) to attach the multilayer fabric to human tissue. An indicator is attached to the multilayer fabric. The indicator provides stretch or pressure feedback indicative of the pressure the multilayer fabric is applying to the wounded tissue. The indicator provides invaluable information for identifying an ideal and medically efficacious amount of compression for individuals with certain underlying conditions that are sensitive to pressure.

In yet another embodiment, the multilayer fabric includes at least three layers. The multilayer fabric includes a hook-and-loop fastener or hook-and-pile fastener (such as VELCRO®) to attach the multilayer fabric to human tissue. A sensor is attached to the multilayer fabric. The sensor provides stretch or pressure feedback indicative of the pressure the multilayer fabric is applying to the wounded tissue. The sensor is usable to apply specific pressure as desired and provides maximum control over desired pressure. This embodiment is useful in research, diagnosis, and adjunctive therapy.

In still yet another embodiment, the multilayer fabric comprises at least three layers. At least one of the layers includes a medicated dressing layer. At least another of the layers includes a printed flexible circuit structure having an array of sensors and an element taken from the group consisting of a heating element that supplies heat to wounded tissue, a vibrating element that supplies vibration to wounded tissue, an electrical stimulation element that provides electrical stimulation to the wounded tissue, and a treatment modality element consistent with another treatment modality. In another embodiment, at least one layer of the multilayer fabric includes at least of an antimicrobial agent, an antiviral agent, or an antifungal agent.

Although certain specific embodiments are described above in order to illustrate the invention, the invention is not limited to the specific embodiments. For additional information on the structure and operation of the multilayer fabrics 10 and 310, and how to construct the multilayer fabrics 10 and 310, see: U.S. Provisional Application Ser. No. 62/903,612, entitled "Multilayer Garments Worn During Wound Care," filed Sep. 20, 2019, by McCain (the entire subject matter of which is incorporated herein by reference). Accordingly, various modifications, adaptations, and combinations of various features of the described embodiments can be practiced without departing from the scope of the invention as set forth in the claims.

What is claimed is:

1. A multilayer fabric bandage for covering wounded tissue consisting of:
   a first layer, wherein the first layer has a tissue contact surface and consists of 90% poly and 10% percent spandex or 73% poly and 27% spandex;
   a second layer consisting of natural fibers, wherein the second layer receives and stores moisture from the tissue, and wherein the tissue moisture is received through the first layer; and
   a third layer of woven fabric, wherein the third layer has an external environment contact surface, and wherein the second layer is disposed between the first layer and third layer;
   wherein the multilayer fabric bandage forms an entirety of a garment enabled to be worn against skin of a user and the first layer is configured to provide compression to wounded tissue on areas of the user the garment covers.

2. The multilayer fabric bandage of claim 1, wherein a surface of the second layer contacts a surface of the first layer that is opposite the tissue contact surface.

3. The multilayer fabric bandage of claim 1, wherein a surface of the second layer contacts a surface of the third layer that is opposite the external environment contact surface.

4. The multilayer fabric bandage of claim 1, wherein no body fluid or blood leaks through to the external environment contact surface.

5. The multilayer fabric bandage of claim 1, wherein the tissue contact surface does not stick to tissue.

6. The multilayer fabric bandage of claim 1, wherein the first layer draws moisture away from wounded tissue and transfers the moisture into the second layer.

7. The multilayer fabric bandage of claim 1, wherein multilayer fabric is part of a garment, and wherein the multilayer fabric is present along only a portion of the garment.

8. The multilayer fabric bandage of claim 1, wherein the tissue contact surface contacts human tissue or animal tissue.

9. The multilayer fabric bandage of claim 1, wherein at least one layer of the multilayer fabric comprises at least one of an antimicrobial agent, an antiviral agent, or an antifungal agent.

10. A method comprising:
  forming a multilayer fabric bandage having a first layer consisting of 90% poly and 10% percent spandex or 73% poly and 27% spandex, a second layer consisting of natural fibers, and a third layer consisting of a wove fabric;
  inserting the second layer between the first layer and the third layer forming an entirety of a garment configured to be worn against skin of a user from the bandage;
  contacting a non-stick skin surface of the first layer to damaged tissue of a user while the user wears the garment;
  compressing the damaged tissue by the first layer; and
  receiving and storing moisture from the damaged tissue by the second layer received through the first layer, and the third layer prevents the moisture from traversing to an outer surface of the third layer.

11. The method of claim 10, further comprising:
  applying at least one of an antimicrobial agent, an antiviral agent, or an antifungal agent to at least one layer of the multilayer fabric.

* * * * *